(12) United States Patent
Oberlander et al.

(10) Patent No.: US 10,357,288 B2
(45) Date of Patent: Jul. 23, 2019

(54) ARTICULATING SPINAL CROSSLINK APPARATUS

(71) Applicants: Eric Oberlander, Baton Rouge, LA (US); Bret Michael Berry, Tallahassee, FL (US)

(72) Inventors: Eric Oberlander, Baton Rouge, LA (US); Bret Michael Berry, Tallahassee, FL (US)

( * ) Notice: Subject to any disclaimer, the term of this patent is extended or adjusted under 35 U.S.C. 154(b) by 104 days.

(21) Appl. No.: 15/351,483

(22) Filed: Nov. 15, 2016

(65) Prior Publication Data

US 2017/0079690 A1 Mar. 23, 2017

Related U.S. Application Data

(63) Continuation of application No. 14/861,743, filed on Sep. 22, 2015.

(51) Int. Cl.
*A61B 17/70* (2006.01)
*A61B 17/68* (2006.01)
*A61B 17/56* (2006.01)

(52) U.S. Cl.
CPC ...... *A61B 17/7037* (2013.01); *A61B 17/7011* (2013.01); *A61B 17/7043* (2013.01); *A61B 17/7052* (2013.01); *A61B 2017/567* (2013.01); *A61B 2017/681* (2013.01); *A61B 2017/7073* (2013.01)

(58) Field of Classification Search
CPC ............ A61B 17/7037; A61B 17/7052; A61B 2017/681
See application file for complete search history.

(56) References Cited

U.S. PATENT DOCUMENTS

| | | | | |
|---|---|---|---|---|
| 8,029,543 | B2* | 10/2011 | Young | A61B 17/7052 606/252 |
| 8,920,475 | B1* | 12/2014 | Ziemek | A61B 17/7052 606/267 |
| 2004/0133203 | A1* | 7/2004 | Young | A61B 17/7052 606/253 |
| 2007/0270809 | A1* | 11/2007 | Drewry | A61B 17/7052 606/279 |
| 2010/0094345 | A1* | 4/2010 | Saidha | A61B 17/7052 606/250 |
| 2012/0150230 | A1* | 6/2012 | Felix | A61B 17/7049 606/250 |
| 2012/0226316 | A1* | 9/2012 | Dant | A61B 17/7007 606/250 |
| 2016/0128734 | A1* | 5/2016 | Barlett | A61B 17/7052 606/253 |
| 2017/0065306 | A1* | 3/2017 | Fauth | A61F 2/4405 |

* cited by examiner

*Primary Examiner* — Ellen C Hammond
(74) *Attorney, Agent, or Firm* — James M. Smedley LLC; James Michael Smedley, Esq.

(57) ABSTRACT

The present invention generally relates to a crosslink for linking a pair of rods in a spinal fusion construct. Specifically, this invention relates to an articulating crosslink that attaches directly to the head of a pedicle screw.

10 Claims, 7 Drawing Sheets

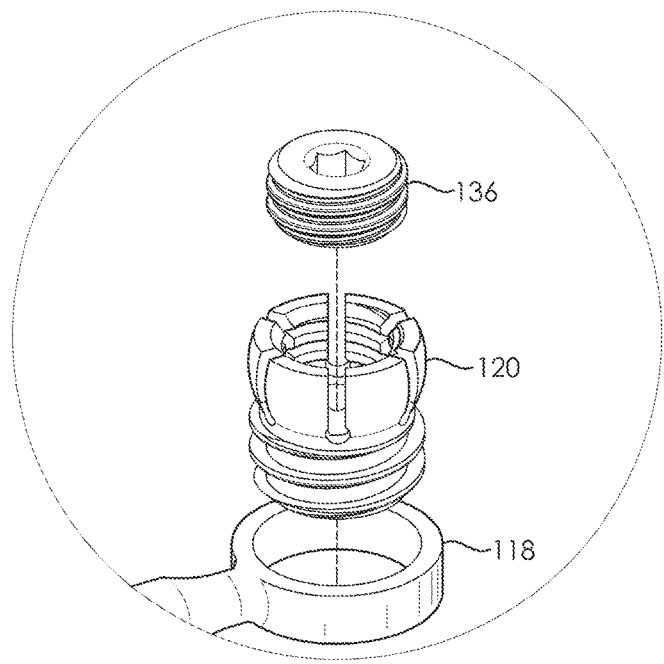
FIG. 5
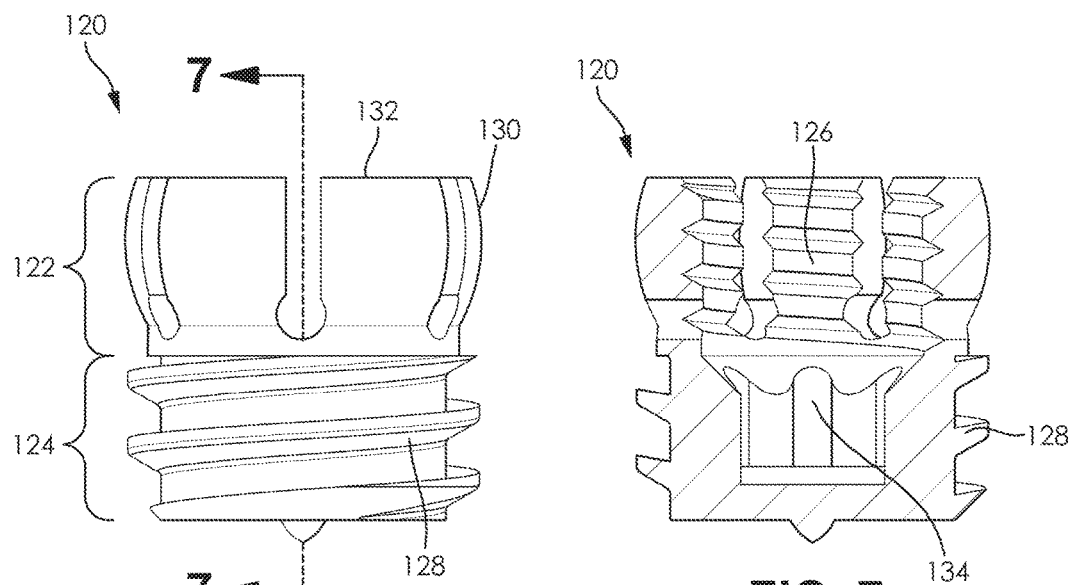
FIG. 6
FIG. 7

ARTICULATING SPINAL CROSSLINK APPARATUS

FIELD OF THE INVENTION

The present invention generally relates to a crosslink for linking a pair of rods in a spinal fusion construct. Specifically, this invention relates to an articulating crosslink that attaches directly to the head of a pedicle screw.

BACKGROUND OF THE INVENTION

A crosslink is commonly used in a spinal fusion construct to connect rods that are on opposite sides of the spine. Currently available crosslink apparatuses are difficult to work with and suffer from design flaws that can lead to the other components of a spinal fusion construct becoming loose. In particular, currently available crosslinks have very limited range of motion incorporated into their structure. This design limitation can make a crosslink difficult for a surgeon to properly align and connect with the other elements of the spinal fusion construct. Additionally, currently available crosslinks attach to the pedicle screws of a spinal fusion construct in such a way that causes the expansion of the head of the pedicle screw and can lead to a loosening of the rod from the pedicle screw.

Therefore, there is a need in the art for an articulating crosslink apparatus that can securely attach to a pedicle screw without expanding the head of the pedicle screw and allow for articulation of the crosslink apparatus for an easier alignment and fit. These and other features and advantages of the present invention will be explained and will become obvious to one skilled in the art through the summary of the invention that follows.

SUMMARY OF THE INVENTION

Accordingly, embodiments of the present invention are directed to providing an articulating crosslink apparatus for linking a pair of rods in a spinal fusion construct. Embodiments of the present invention may include at least one ball joint that allows for spherical articulation of the arms of the crosslink and an expandable collet.

According to an embodiment of the present invention, a crosslink apparatus for linking at least two rods in a spinal fusion construct, the crosslink comprising: an articulating joint formed with one or more ball joint sockets and one or more joint locking points, a ball joint retained by each of the ball joint sockets, and a joint locking element for each of the joint locking points, wherein the joint locking element secures the ball joint within the articulating joint body.

According to an embodiment of the present invention, the articulating joint is further formed with a first crosslink arm that is integrated upon the articulating joint.

According to an embodiment of the present invention, the articulating joint is further configured with a crosslink arm receiving cylinder that permits a second crosslink arm to adjustably slide within the ball joint that is retained within the articulating joint.

According to an embodiment of the present invention, one of the one or more ball joint sockets is formed at the intersection of the joint locking point and the crosslink arm receiving cylinder.

According to an embodiment of the present invention, the articulating joint is formed with two ball joints sockets each of which is configured to engage with a ball joint.

According to an embodiment of the present invention, the ball joint is a ball joint connector comprised of ball joint head portion that is configured to engage with one of the ball joint sockets and a crosslink arm connector portion that is configured to attach to a crosslink arm and permit the crosslink arm to adjustably slide through the crosslink arm connector portion.

According to an embodiment of the present invention, a crosslink apparatus for linking at least two rods in a spinal fusion construct, the crosslink comprising: an articulating joint formed with a ball joint socket, a joint locking point, a crosslink arm that is integrated upon the articulating joint, and a crosslink arm receiving cylinder that permits a second crosslink arm to adjustably slide within the articulating joint, wherein the ball joint socket is formed at the intersection of the joint locking point and the crosslink arm receiving cylinder, a ball joint retained by ball joint socket and adapted to receive the second crosslink arm, and a joint locking element for the joint locking point, wherein the joint locking element secures the ball joint and the second crosslink arm within the articulating joint body.

According to an embodiment of the present invention, a crosslink apparatus for linking at least two rods in a spinal fusion construct, the crosslink apparatus comprising: an articulating joint with a joint locking element, a first crosslink arm and a second crosslink arm extending from the articulating joint, an attachment collar on the first crosslink arm that is adapted to receive an expandable collet, and a collet securing means that fastens to the expandable collet to cause the expandable collet to engage with the attachment collar.

According to an embodiment of the present invention, the articulating joint is comprised of a single ball joint that is configured to permit the first crosslink arm to adjustably slide within the articulating joint.

According to an embodiment of the present invention, the joint locking element is a joint set screw that secures the first crosslink arm in place within the single ball joint.

According to an embodiment of the present invention, the articulating joint is a double ball joint configured with two ball joint sockets each of which are configured to engage with a ball joint head portion of a ball joint connector that allows for spherical articulation of the crosslink arms.

According to an embodiment of the present invention, the ball joint connectors is further comprised of a crosslink arm connector portion that is configured to permit each of the crosslink arms to adjustably slide through the ball joint connector.

According to an embodiment of the present invention, the joint locking element is a joint set screw in each of the ball joint sockets that secures the crosslink arms in place via the ball joint connector on each of the crosslink arms.

According to an embodiment of the present invention, the second crosslink arm is further comprised of an attachment collar on the second crosslink arm that is adapted to receive an expandable collet.

According to an embodiment of the present invention, the second crosslink arm is further comprised of a hooked connector on the second crosslink arm.

According to an embodiment of the present invention, the expandable collet is comprised of an upper portion configured with internal threading and a lower portion configured with external threading.

According to an embodiment of the present invention, the upper portion of the expandable collet has a curved external surface.

According to an embodiment of the present invention, the upper portion of the expandable collet is divided into a plurality of sections that expand to engage with the attachment collar when the collet securing means is a fastened to the expandable collet.

According to an embodiment of the present invention, the collet securing means is a collet set screw that expands the expandable collet to engage with the attachment collar.

According to an embodiment of the present invention, the expandable collet is comprised of an internal driver feature formed within the expandable collet.

The foregoing summary of the present invention with the preferred embodiments should not be construed to limit the scope of the invention. It should be understood and obvious to one skilled in the art that the embodiments of the invention thus described may be further modified without departing from the spirit and scope of the invention.

BRIEF DESCRIPTION OF THE DRAWINGS

FIG. 5 is a detailed exploded view of a crosslink arm of an articulating spinal crosslink apparatus in accordance with an embodiment of the present invention;

FIG. 6 is front view of an expandable collet in accordance with an embodiment of the present invention;

FIG. 7 is a cross-sectional view of an expandable collet in accordance with an embodiment of the present invention;

DETAILED SPECIFICATION

Figure 1:
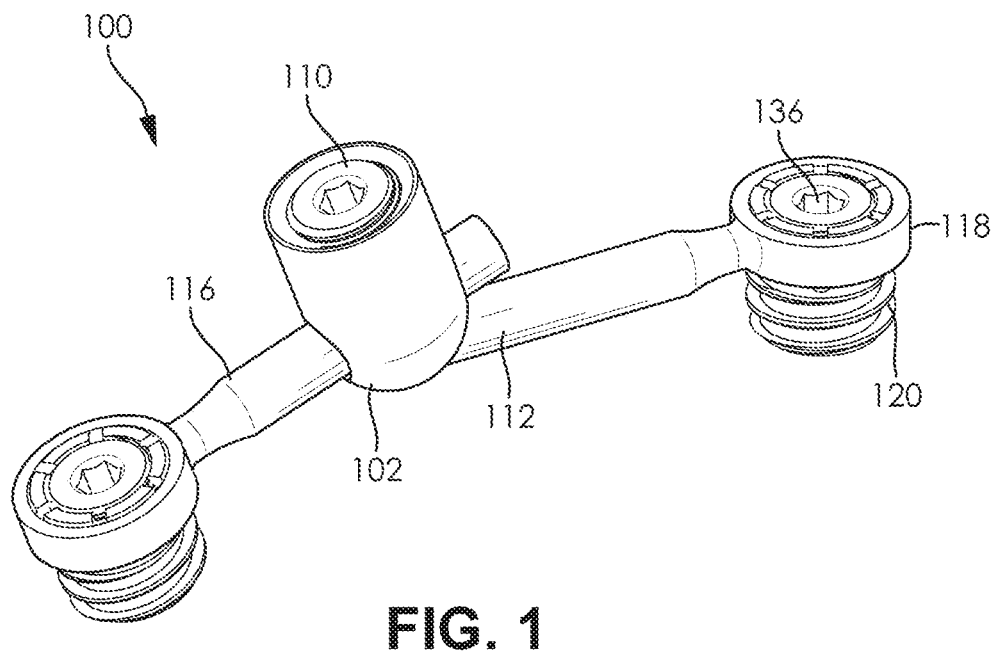
FIG. 1 is a perspective view of an articulating spinal crosslink apparatus with a single joint in accordance with an embodiment of the present invention.

The present invention generally relates to a crosslink for linking a pair of rods in a spinal fusion construct. Specifically, this invention relates to an articulating crosslink that attaches directly to the head of a pedicle screw.

According to an embodiment of the present invention, a spinal crosslink apparatus is comprised of an articulating joint, a joint locking element, a plurality of crosslink arms, an attachment collar, an expandable collet, and a collet securing means. Another optional component in some embodiments of the present invention may be a hooked connector. Some embodiments of the present invention may include fewer or additional components depending on the specific application of the spinal crosslink apparatus. One of ordinary skill in the art would appreciate there are many possible configurations and components that might be used for a spinal crosslink apparatus, and embodiments of the present invention are contemplated for use with any such configuration or component.

According to an embodiment of the present invention, the spinal crosslink apparatus is constructed from a variety of durable materials. In a preferred embodiment, the majority of the components of the spinal crosslink apparatus are comprised of any variety of metals and metal alloys suitable for use inside the human body. Examples of suitable metals include, but are not limited to, titanium alloy, pure titanium, stainless steel, and cobalt chrome. In some embodiments, components of the spinal crosslink apparatus may be comprised of various plastics, including, but not limited to, polyether ether ketone ("PEEK"). In the preferred embodiment, the various components of the spinal crosslink apparatus are constructed from specific materials based upon the application or function of that component. One of ordinary skill the art would appreciate that there are numerous suitable materials from which the components of the spinal crosslink apparatus could be constructed, and embodiments of the present invention are contemplated for use with any such material.

According to an embodiment of the present invention, the articulating joint may be a single ball joint that allows for spherical articulation of the crosslink arms. In a preferred embodiment, the single ball articulating joint is comprised of a center ball joint and a main joint body that is formed with a ball joint socket, a joint locking point, a crosslink arm receiving cylinder, and one integrated crosslink arm that extends from the bottom of the main joint body. In this embodiment, the integrated crosslink arm is of a fixed length, but may be rotatable around the main joint body. The joint locking point is a cavity formed in the top of the main joint body that is configured to receive a joint locking element. In this embodiment, the crosslink arm receiving cylinder is a channel that transects the main joint body and is adapted to receive an additional crosslink arm. Likewise, the center ball joint is also configured with an opening that receives the additional crosslink arm. In this embodiment, the center ball joint is retained by a ball joint socket that is formed by the intersection of the joint locking point and the crosslink arm receiving cylinder. The center ball joint enables the spherical articulation of the crosslink arms. One of ordinary skill in the art would appreciate that there are many possible configurations for a single jointed embodiment of an articulating joint, and embodiments of the present invention are contemplated for use with any such configuration.

According to an embodiment of the present invention, the articulating joint may be a double ball joint that allows for spherical articulation of the crosslink arms. In a preferred embodiment, the double ball articulating joint is comprised of a two ball joint connectors and a main joint body that is formed with two ball joint sockets and two joint locking points. In this embodiment, each joint locking point is a cavity formed in the top of the main joint body that is configured to receive a joint locking element. Similarly, each ball joint socket is formed in the bottom of the main joint body and is configured to retain one of the ball joint connectors. Furthermore, a portion of the ball joint connector protrudes from the main joint body and is configured to connect with a crosslink arm. One of ordinary skill in the art would appreciate that there are many possible configurations for a double jointed embodiment of an articulating joint, and embodiments of the present invention are contemplated for use with any such configuration. Furthermore, one of ordinary skill would appreciate that the articulating joint could be configured with additional jointing for other applications without departing from the spirit and scope of the present invention.

According to an embodiment of the present invention, the articulating joint may be comprised of a main joint body. In a first preferred embodiment, the main joint body is a single jointed component. In the single jointed embodiment, the main joint body may be formed with a joint locking point, a crosslink arm receiving cylinder, and an integrated crosslink arm that extends from the main joint body. The single jointed embodiment may be further comprised of a single ball joint and a joint locking element. In the single jointed embodiment, the single ball joint may be retained within a ball joint socket formed by the intersection of the joint locking point and the crosslink arm receiving cylinder, while the joint locking element is adapted to engage with the joint locking point. In a second preferred embodiment, the main joint body is a double jointed component. In the double jointed embodiment, the main joint body may be formed with two ball joint sockets and two joint locking points. The double jointed embodiment may be further comprised of two ball joint connectors and two joint locking elements. In the double jointed embodiment, each ball joint connector is retained by one of the ball joint sockets, while the each joint locking element is adapted to engage with a joint locking point. One of ordinary skill in the art would appreciate there are main suitable designs for a main joint body, and embodiments of the present invention are contemplated for use with any such design.

According to an embodiment of the present invention, main joint body may be formed with one or more joint locking points. In a preferred embodiment, each joint locking point is formed in the top of the main joint body and merges with at least a portion of the ball joint socket. In the preferred embodiment, there is one joint locking point to correspond to the number of joints on the main joint body. For example, in a single jointed embodiment there is one joint locking point, while in a double jointed embodiment there are two joint locking points. In the preferred embodiment, the joint locking point is adapted to receive a joint locking element. In alternate embodiments, the joint locking points may be formed in alternate areas of the main joint body as may be necessary by the design of the main joint body. Additionally, the number of joint locking points may not directly correlate with the number of joints on the main joint body. For example, in some embodiments, there may only be one joint locking point for multiple joints. One or ordinary skill in the art would appreciate that there are many suitable arrangements for a one or more joint locking elements on a main joint body, and embodiments of the present invention are contemplated for use with any such arrangement.

According to an embodiment of the present invention, each joint locking point is adapted to receive a joint locking element. In a preferred embodiment, the joint locking element is a set screw that engages with the joint locking point. In the preferred embodiment, the joint locking element secures each joint of the articulating joint by engaging with the ball joint or ball joint connector that is retained by the ball joint socket. As an illustrative example, the joint locking element engages with the joint locking point and is tightened until the joint locking element secures the ball joint or ball joint connector within the ball joint socket, thereby stabilizing the joint and any crosslink arm that may also be connected. In an alternate embodiment the joint locking element may be any other suitable fastener that can secure the joint. One or ordinary skill in the art would appreciate there are many suitable designs for a joint locking element, and embodiments of the present invention are contemplated for use with any such design.

According to an embodiment of the present invention, the main joint body may be formed with one or more ball joint sockets. In a preferred embodiment, each ball joint socket is configured to retain a ball joint. In the preferred embodiment, the combination of the ball joint and the ball joint socket allow for spherical articulation of the crosslink arms that are connected to the crosslink apparatus. The ball joint socket may be continuously formed with at least a portion of the joint locking point so as to allow the joint locking element to secure the ball joint within the ball joint socket. In the preferred embodiment of the single jointed main joint body, the ball joint socket is formed by the intersection of the joint locking point and the crosslink arm receiving cylinder. In the preferred embodiment of the double jointed main body, the ball joint sockets are formed on the bottom of the main joint body. In alternate embodiments the ball joint sockets may be formed in other areas of the main joint body as is necessary by design or application. One of ordinary skill in the art would appreciate that there are many suitable arrangements for the one or more ball joints sockets, and embodiments of the present invention are contemplated for use with any such arrangement.

According to an embodiment of the present invention, the ball joint socket is configured to receive a ball joint. In a first preferred embodiment, the ball joint may be a spherical component that is configured with a cavity or similar opening that transects the body of the spherical component. In this first preferred embodiment, the cavity in the spherical component is adapted to receive a crosslink arm. This embodiment will typically be used in the single jointed embodiment of the main joint body, but may also be appropriate in other embodiments depending on the design of the main joint body. In the single jointed embodiment of the main joint body, the ball joint is positioned in the ball joint socket so that the hole in the ball joint aligns with the crosslink arm receiving cylinder. This arrangement allows for the crosslink arm to adjustably slide through the main joint body and the ball joint. Upon appropriate adjustment, the joint locking element may be secured in place on the ball joint so as to prevent the crosslink arm from sliding out of the main joint body and to prevent unwanted movement of the joint. One of ordinary skill in the art would appreciate that there are many suitable designs for a spherical ball joint and embodiments of the present invention are contemplated for use with any such design.

According to an embodiment of the present invention, the ball joint may be a ball joint connector. In a preferred embodiment, the ball joint connector is comprised of an upper ball joint head portion and a lower crosslink arm connector portion. The ball joint connector embodiment of the ball joint will typically be used in the double jointed embodiment of the main joint body, but may also be appropriate in other embodiments depending on the design of the main joint body. In the preferred embodiment, the ball joint head portion is retained by one of the ball joint sockets on the main joint body, while the crosslink arm connector portion protrudes from the bottom of the main joint body. The ball joint head portion enables the spherical articulation of any crosslink arm that is connected to the main joint body via the ball joint connector. The crosslink connector portion attaches to a crosslink arm and allows for the crosslink arm to adjustably slide back and forth maximizing the customization and arrangement options of the crosslink apparatus. Upon appropriate adjustment, the joint locking element may be secured upon the ball joint connector. This action will cause the ball joint head portion of the ball joint connector to be firmly secured within the ball joint socket to prevent unwanted movement of the joint and will also cause the crosslink arm connector portion to tighten around the crosslink arm to prevent the crosslink arm from sliding out of the ball joint connector. One of ordinary skill in the art would appreciate that there are many suitable designs for a ball joint connector and embodiments of the present invention are contemplated for use with any such design.

According to an embodiment of the present invention, the main joint body may be formed with a one or more crosslink arm receiving cylinders. In a preferred embodiment, the crosslink arm receiving cylinder is a channel that goes through the side wall of the main joint body. The crosslink arm receiving cylinder is typically used on single jointed embodiments of the articulating joint, but may also be appropriate in other embodiments depending on the design of the main joint body. In the preferred embodiment, the crosslink arm receiving cylinder is adapted to receive a crosslink arm and permit the crosslink arm to adjustably slide within the main joint body. The crosslink arm receiving cylinder may intersect with the joint locking point to form a ball joint socket at such intersection. In the preferred embodiment, the joint locking element will engage with the ball joint in the ball joint socket to secure the crosslink arm within the crosslink arm receiving cylinder and prevent the crosslink arm from sliding out of the main joint body. In alternate embodiments of the invention, the crosslink arm receiving cylinder may be located through any suitable portion of the main joint body. Similarly, the use of the word cylinder does not necessarily imply that the crosslink arm receiving cylinder will have a cylindrical shape. In a preferred embodiment, the crosslink arm receiving cylinder will have a shape to match that of the crosslink arm, which may include, but is not limited to, cylindrical, triangular, rectangular, and squared shapes. One of ordinary skill in the art would appreciate that there are many suitable arrangements for a crosslink arm receiving cylinder and embodiments of the present invention are contemplated for use with any such arrangement.

According to an embodiment of the present invention, the spinal crosslink apparatus may be comprised of one or more crosslink arms. In a preferred embodiment each crosslink arm extends from the main joint body. In some embodiments, the crosslink arm is fully integrated upon and forms a part of the main joint body. In some embodiments, the crosslink arm is a separate component that attaches to the main joint body via the crosslink arm receiving cylinder or the ball joint connector. In such an embodiment, the length of the crosslink can be adjusted by sliding the crosslink arm through the crosslink arm receiving cylinder or the ball joint connector. In some embodiments, the articulating joint will include both an integrated crosslink arm and a detachable crosslink arm. In the preferred embodiment, each crosslink arm includes both a first end that may be permanently fixed to or configured to detachably connect with the main joint body and a second end that is configured with an arm connector portion. Furthermore, because each of the crosslink arms are directly or indirectly attached to a ball joint, the crosslink arms may be articulated in a spherical manner to allow for the crosslink apparatus to be adjusted to a particular application. While many different lengths of crosslink arms are possible, the crosslink apparatus can typically be adjusted and expanded to cover up to twice its shortest length. One of ordinary skill in the art would appreciate there any many possible designs and arrangements for crosslink arms, and embodiments of the present invention are contemplated for use with any such design or arrangement.

According to an embodiment of the present invention, the crosslink arms may include an arm connector portion. In a preferred embodiment, the arm connector portion is an attachment collar that is configured to receive and engage with an expandable collet. In the preferred embodiment the attachment collar is a ring that goes around a portion of the expandable collet. In an alternate preferred embodiment, the arm connector portion is a hooked connector that is adapted to connect directly to a fusion rod of a spinal fusion construct. The hooked connector may also include a rod locking element, such as a set screw, that locks the hooked connector onto the fusion rod. One of ordinary skill in the art would appreciate that there are many suitable designs and configurations for an arm connector portion, and embodiments of the present invention are contemplated for use with any such design or configuration.

According to an embodiment of the present invention, the spinal crosslink apparatus may be comprised of one or more expandable collets. In a preferred embodiment, the expandable collet is comprised of an upper portion that engages with the attachment collar of a crosslink arm and a lower portion that engages with the head of a pedicle screw. The expandable collet may also be comprised of a collet securing means that engages with the upper portion of the expandable collet to cause the expandable collet to engage with the attachment collar of a crosslink arm. One of ordinary skill in the art would appreciate that there are many suitable designs for an expandable collet, and embodiments of the present invention are contemplated for use with any such design.

According to an embodiment of the present invention, the expandable collet is comprised of an upper portion. In a preferred embodiment, the inner wall of the upper portion of the expandable collet is configured with threading (or internal threading) that is adapted to engage with the collect securing means. Additionally, the outer wall of the upper portion may have a curved or rounded surface to allow the expandable collet to have some degree of articulation with the attachment collar of a crosslink arm. This feature allows the crosslink arm to have some degree of adjustment and permits the spinal crosslink apparatus to have a better fit as the crosslink arm is not required to lock in a specific alignment around the expandable collet. In the preferred embodiment, the upper portion of the expandable collet may be divided into a plurality of sections that expand to engage with the attachment collar of the crosslink arm. The expansion of these sections is caused by the collet securing means being fastened to the upper portion of the expandable collet. In a preferred embodiment, the collet securing means is a set screw that engages with the internal threading of the upper portion of the expandable collet thereby causing the sections of expandable collet to expand and engage with the attachment collar of the crosslink arm. One of ordinary skill in the art would appreciate that there are many possible configurations for the upper portion of an expandable collet, and embodiments of the present invention are contemplated for use with any such configuration.

According to an embodiment of the present invention, the expandable collet is comprised of a lower portion. In a preferred embodiment, the outer wall of the lower portion of the expandable collet is configured with threading (or the external threading) that is adapted to engage with the head of a pedicle screw. The expandable collet may also be configured with an internal driver feature that is formed within the expandable collet. In a preferred embodiment, the internal driver feature is formed in the bottom center of the interior of the expandable collet. The internal driver feature is adapted to allow a tool to be used to tighten the expandable collet onto the head of a pedicle screw. One of ordinary skill in the art would appreciate that there are many possible configurations for the lower portion of an expandable collet, and embodiments of the present invention are contemplated for use with any such configuration.

EXEMPLARY EMBODIMENTS

Turning now to FIG. 1, a perspective view of an articulating spinal crosslink apparatus with a single joint in accordance with an embodiment of the present invention. In a preferred embodiment, the articulating spinal crosslink apparatus 100 is comprised of a single jointed main joint body 102. In the single jointed embodiment one crosslink arm 112 is integrated upon the main joint body 102, while the other crosslink arm 116 adjustably slides through the center of the main joint body 102 via a crosslink arm receiving cylinder (not shown). At the end of each crosslink arm 112, 116 there is an attachment collar 118. The attachment collar 118 is configured to receive the expandable collet 120. The collet securing means 136 engages with an upper portion of the expandable collet 120 to firmly secure the expandable collet 120 within the attachment collar 118. The joint locking element 110 is used to secure the ball joint (not shown) inside the main joint body 102 and to prevent unwanted articulation of the articulating spinal crosslink apparatus 100. The joint locking element 110 is also used to secure the adjustable crosslink arm 116 within the crosslink arm receiving cylinder (not shown), to prevent the adjustable crosslink arm 116 from sliding out of the main joint body 102.

Figure 2:
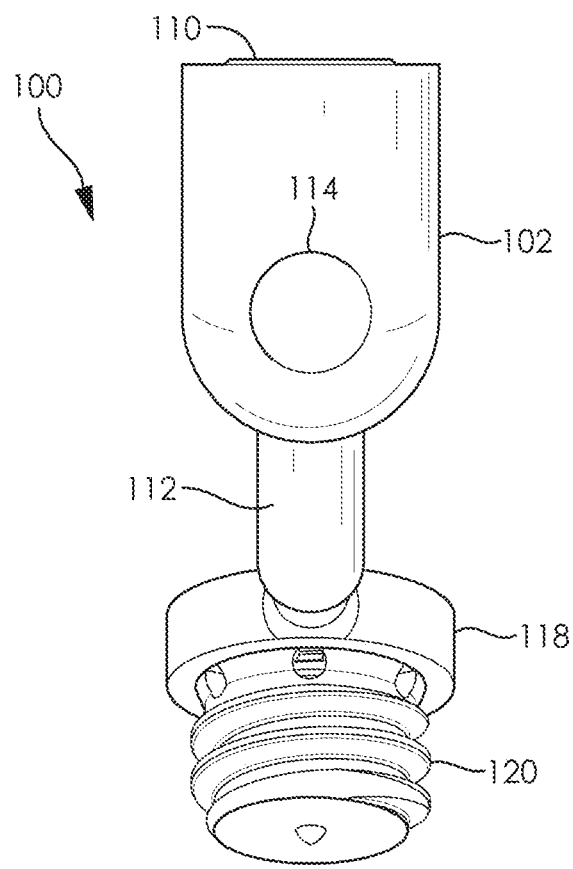
FIG. 2 is a front view of a main joint body of an articulating spinal crosslink apparatus with a single joint in accordance with an embodiment of the present invention.

Turning now to FIG. 2, a front view of a main joint body of an articulating spinal crosslink apparatus with a single joint in accordance with an embodiment of the present invention. In a preferred embodiment, the articulating spinal crosslink apparatus 100 is primarily comprised of a single jointed main joint body 102. In the single jointed embodiment one crosslink arm 112 is integrated upon the main joint body 102, while the other crosslink arm (not shown) adjustably slides through the center of the main joint body 102 via a crosslink arm receiving cylinder 114. The joint locking element 110 is used to secure the adjustable crosslink arm (not shown) within the crosslink arm receiving cylinder 114, to prevent the adjustable crosslink arm (not shown) from sliding out of the main joint body 102.

Figure 3:
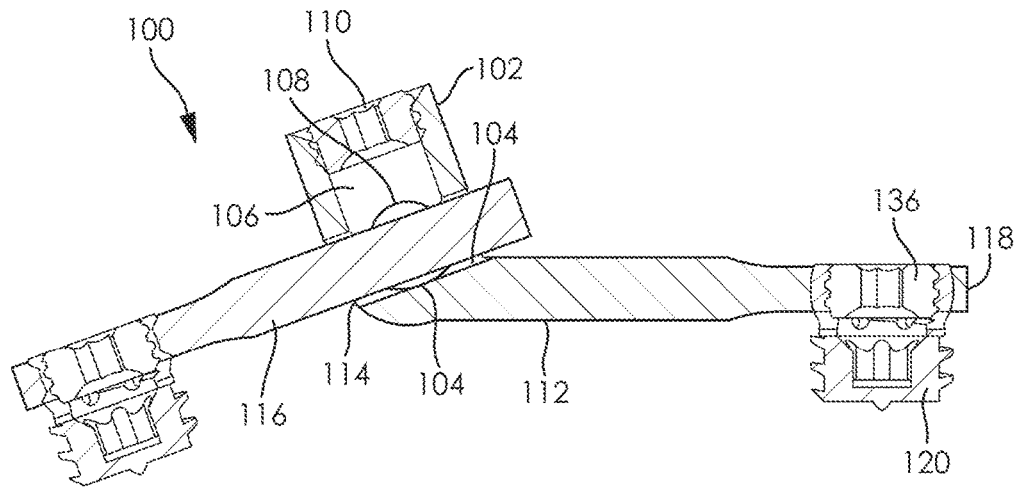
FIG. 3 is a cross-sectional view of an articulating spinal crosslink apparatus with a single joint in accordance with an embodiment of the present invention.

Turning now to FIG. 3 is a cross-sectional view of an articulating spinal crosslink apparatus with a single joint in accordance with an embodiment of the present invention. In a preferred embodiment, the articulating spinal crosslink apparatus 100 is comprised of a single jointed main joint body 102. The main joint body 102 is formed with a joint locking point 106 in the top of the main joint body 102 and a crosslink arm receiving cylinder 114 in the side of the main joint body 102. At the intersection of the joint locking point 106 and crosslink arm receiving cylinder 114 a ball joint socket 104 is formed that holds the ball joint 108. In the single jointed embodiment one crosslink arm 112 is integrated upon the main joint body 102, while the other crosslink arm 116 adjustably slides through the center of the main joint body 102 via a crosslink arm receiving cylinder 114. The adjustable crosslink arm 116 slides back and forth within the crosslink arm receiving cylinder 114 and a hole formed in the ball joint 108. The joint locking element 110 engages with the ball joint 108 via the joint locking point 106 to secure the ball joint 108. Securing the ball joint 108 simultaneously prevents the articulation of the crosslink arms about the main joint body 102 and fixes the adjustable crosslink arm 116 in place to prevent the adjustable crosslink arm 116 from sliding out of the main joint body 102. At the end of each crosslink arm 112, 116 there is an attachment collar 118. The attachment collar 118 is configured to receive the expandable collet 120. The collet securing means 136 engages with an upper portion of the expandable collet 120 to firmly secure the expandable collet within the attachment collar 118.

Figure 4:
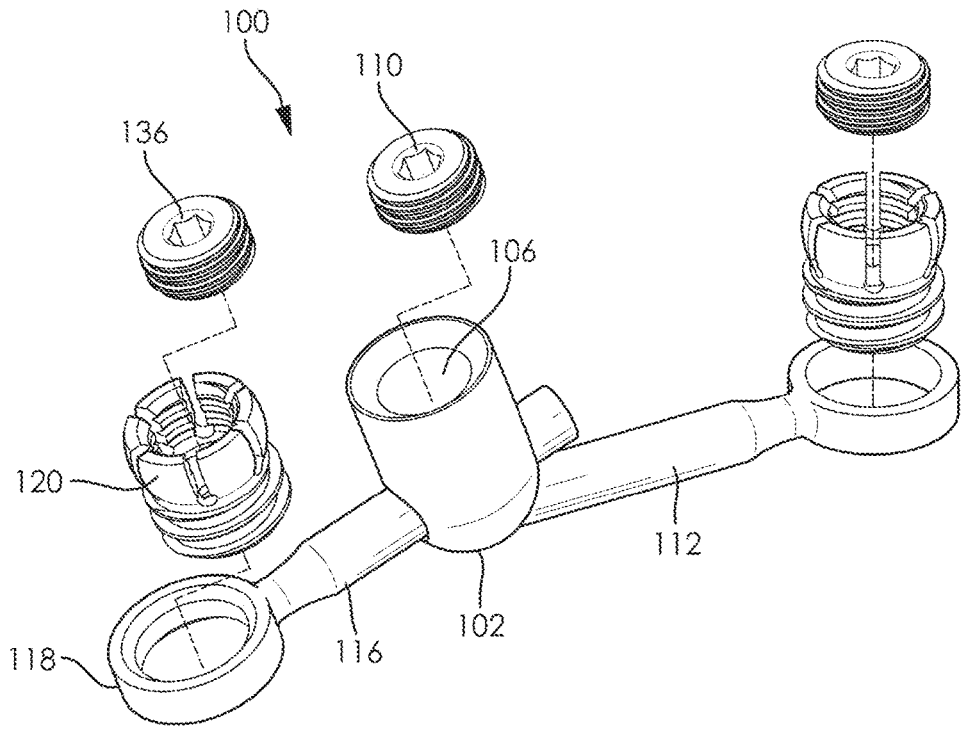
FIG. 4 is an exploded view of an articulating spinal crosslink apparatus with a single joint in accordance with an embodiment of the present invention.

Turning now to FIG. 4, an exploded view of an articulating spinal crosslink apparatus with a single joint in accordance with an embodiment of the present invention. In a preferred embodiment, each of the crosslink arms 112, 116 extend away from the main joint body 102 of the articulating crosslink apparatus 100. The main joint body 102 is formed with a joint locking point 106 that receives a joint locking element 110. The attachment collar 118 on each of the crosslink arms 112, 116 is each adapted to receive an expandable collet 120. The upper portion of the expandable collet 120 is configured to receive the collet securing means 136.

Turning now to FIG. 5, a detailed exploded view of a crosslink arm of an articulating spinal crosslink apparatus in accordance with an embodiment of the present invention. In a preferred embodiment, the attachment collar 118 is adapted to receive an expandable collet 120. The upper portion of the expandable collet 120 is configured to receive the collet securing means 136.

Turning now to FIG. 6, a front view of an expandable collet in accordance with an embodiment of the present invention. In a preferred embodiment, the expandable collet 120 is comprised an upper portion 122 that is divided into a plurality of sections 132 that expand to engage with the inner surface of the attachment collar (not shown) when the collet securing means (not shown) is fastened to the expandable collet 120. The expandable collet is also comprised of a lower portion 124 that has external threading 128. The upper portion 122 of the expandable collet 120 has curved external surfaces 130.

Turning now to FIG. 7, a cross-sectional view of an expandable collet in accordance with an embodiment of the present invention. In a preferred embodiment, the expandable collet 120 is comprised of an upper portion that has internal threading 126 and a lower portion that has external threading 128. The expandable collet 120 also includes an internal driver feature 134 that is adapted to engage with a tool that tightens the expandable collet 120 on to the head of a pedicle screw (not shown).

Figure 8:
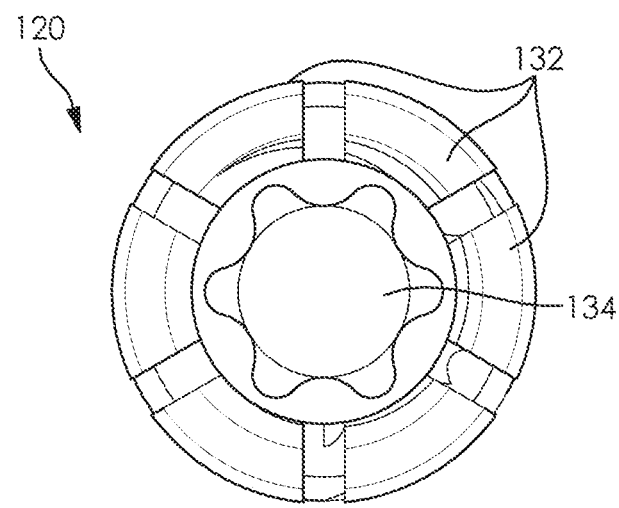
FIG. 8 is a top view of an expandable collet in accordance with an embodiment of the present invention.

Turning now to FIG. 8, a top view of an expandable collet in accordance with an embodiment of the present invention. In a preferred embodiment, the upper portion of the expandable collet 120 is divided into a plurality of sections 132 that can be expanded to engage with the inner surface of the attachment collar (not shown). The expandable collet 120 also includes an internal driver feature 134 formed in the bottom center of the interior of the expandable collet 120.

Figure 9:
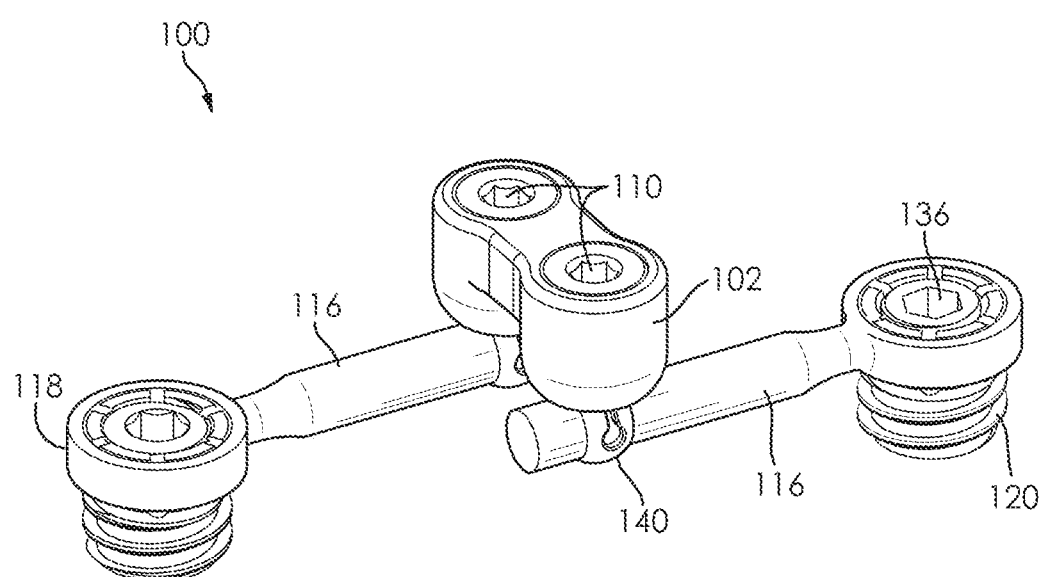
FIG. 9 is a perspective view of an articulating spinal crosslink apparatus with a double joint in accordance with an embodiment of the present invention.

Turning now to FIG. 9, a perspective view of an articulating spinal crosslink apparatus with a double joint in accordance with an embodiment of the present invention. In a preferred embodiment, the articulating spinal crosslink apparatus 100 is comprised of a double jointed main joint body 102. In the double jointed embodiment each crosslink arms 116 adjustably slides through a crosslink arm connector portion of the ball joint connector 140. At the end of each crosslink arm 116 there is an attachment collar 118. The attachment collar 118 is configured to receive the expandable collet 120. The collet securing means 136 engages with an upper portion of the expandable collet 120 to firmly secure the expandable collet within the attachment collar 118. The joint locking element 110 is used to secure the ball joint head portion (not shown) of the ball joint connector 140 inside the main joint body 102 and to prevent unwanted articulation of the articulating spinal crosslink apparatus 100. The joint locking element 110 is also used to secure the adjustable crosslink arms 116 within the crosslink arm connector portion of the ball joint connectors 140, to prevent the adjustable crosslink arms 116 from sliding out of the ball joint connectors 140.

Figure 10:
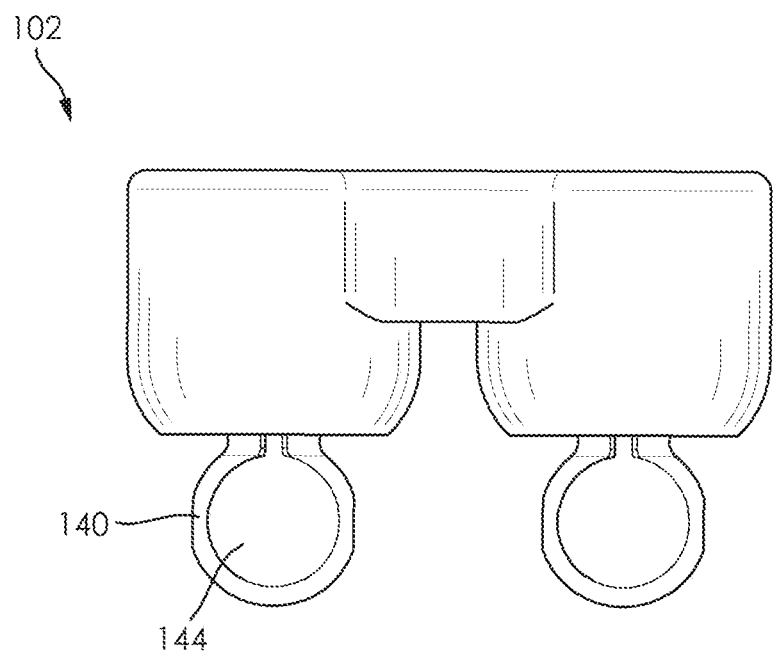
FIG. 10 is a front view of a main joint body of an articulating spinal crosslink apparatus with a double joint in accordance with an embodiment of the present invention.

Turning now to FIG. 10, a front view of a main joint body of an articulating spinal crosslink apparatus with a double joint in accordance with an embodiment of the present invention. In a preferred embodiment, the main joint body 102 retains two ball joint connectors 140. Each ball joint connector 140, is comprised of an upper ball joint head portion (not shown) that is retained within a ball joint socket (not shown) formed inside the main joint body 102 and a lower crosslink arm connector portion 144 that protrudes from the bottom of the main joint body to connect with a crosslink arm (not shown).

Figure 11:
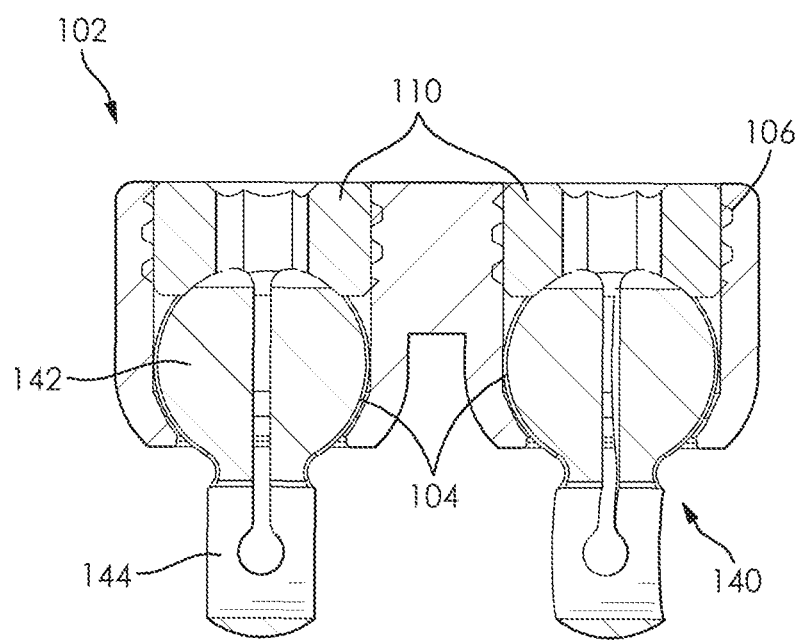
FIG. 11 is a front cross-sectional view of a main joint body of an articulating spinal crosslink apparatus with a double joint in accordance with an embodiment of the present invention.

Turning now to FIG. 11, a front cross-sectional view of a main joint body of an articulating spinal crosslink apparatus with a double joint in accordance with an embodiment of the present invention. In a preferred embodiment, the main joint body 102 retains two ball joint connectors 140 within ball joint sockets 104 formed inside of the main joint body 102. Each ball joint connector 140 is comprised of an upper ball joint head portion 142 that is retained within a ball joint socket 104 and a lower crosslink arm connector portion 144 that extends beyond the bottom of the main joint body 102 to connect with a crosslink arm (not shown). The main joint body is also comprised of two joint locking elements 110 that engage with the ball joint head portions 142 of the ball joint connectors 140 via the joint locking points 106. The engagement of a joint locking element 110 with a ball joint head portion 142 simultaneously secures the ball joint connector 140 within the main joint body 102 and the crosslink arm (not shown) within the crosslink arm connector portion 144 of the ball joint connector 140.

Figure 12:
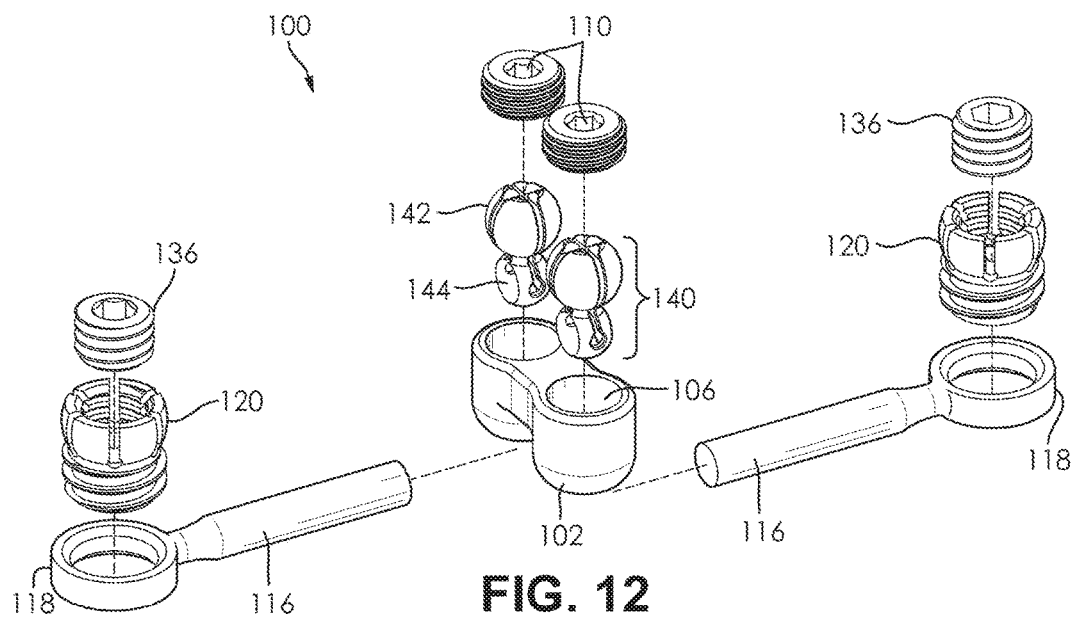
FIG. 12 is an exploded view of an articulating spinal crosslink apparatus with a double joint in accordance with an embodiment of the present invention.

Turning now to FIG. 12, an exploded view of an articulating spinal crosslink apparatus with a double joint in accordance with an embodiment of the present invention. In a preferred embodiment, the articulating spinal crosslink apparatus 100 is comprised of a double jointed main joint body 102. The main joint body 102 is formed with two joint locking points 106 in the top of the main joint body 102. The crosslink arms 116 slide back and forth within the crosslink arm connector portion 144 of the ball joint connector 140. The joint locking element 110 engages with ball joint head portion 142 of the ball joint connectors 140 via the joint locking point 106 to secure the ball joint connectors 140 from articulating with the main joint body 102. Securing the ball joint connectors 140 simultaneously prevents the articulation of the crosslink arms within the main joint body 102 and fixes the adjustable crosslink arm 116 in place to prevent the adjustable crosslink arms 116 from sliding out of the crosslink arm connector portion 144 of the ball joint connector 140. At the end of each crosslink arm 116 there is an attachment collar 118. The attachment collar 118 is configured to receive the expandable collet 120. The collet securing means 136 engages with an upper portion of the expandable collet 120 to firmly secure the expandable collet within the attachment collar 118.

Figure 13:
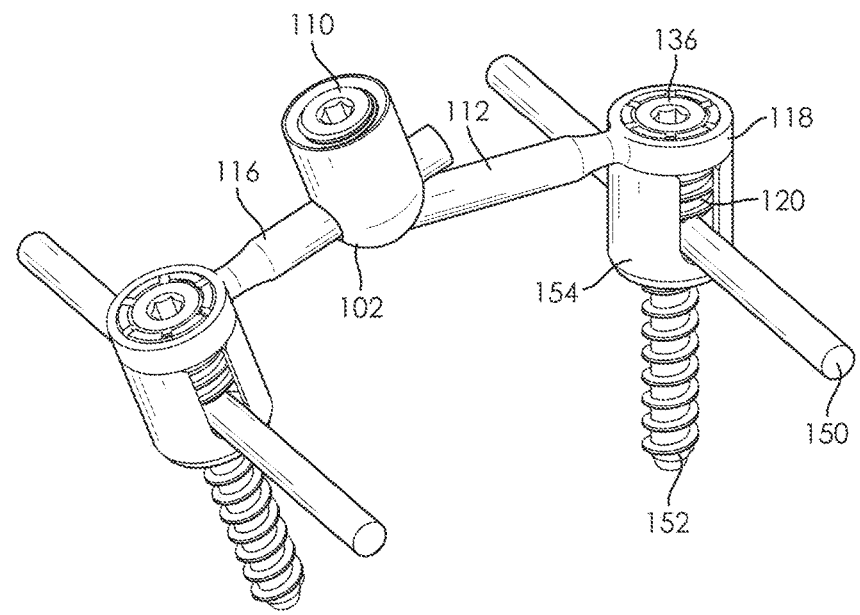
FIG. 13 is an illustration of an articulating spinal crosslink apparatus with a single joint attached to the heads of two pedicle screws of a spinal fusion construct in accordance with an embodiment of the present invention.

Turning now to FIG. 13, an illustration of an articulating spinal crosslink apparatus with a single joint attached to the heads of two pedicle screws of a spinal fusion construct in accordance with an embodiment of the present invention. In a preferred embodiment, the articulating spinal crosslink apparatus 100 is connected to two pedicle screws 152 of a spinal fusion construct. The crosslink arms 112, 116 extend from the main body 102 of the articulating spinal crosslink apparatus 100 to connect with the pedicle screw heads 154. The crosslink arms 112, 116 are attached to the pedicle screws 152 via an expandable collet 120. In practice, the pedicle screw 152 will first be implanted into the patient that is undergoing spinal fusion surgery, followed by the placement of a spinal fusion rod 150 in the groove of the pedicle screw head 154. Next, the lower portion of the expandable collet 120 is secured to the pedicle screw head 154 using an internal driver feature (not shown) formed in the bottom center of the expandable collet 120. This will lock the spinal fusion rod 150 in place within the pedicle screw head 154. Then, the attachment collar 118 of a crosslink arm 112, 116 is placed over and around the upper portion of the expandable collet 120. Subsequently, the collet securing means 136 is attached to the upper portion of the expandable collet 120 to secure the expandable collet 120 within the attachment collar 118. Finally, the joint locking element 110 can be tightened to secure the crosslink arms 112, 116 of the articulating spinal crosslink apparatus 100.

Figure 14:
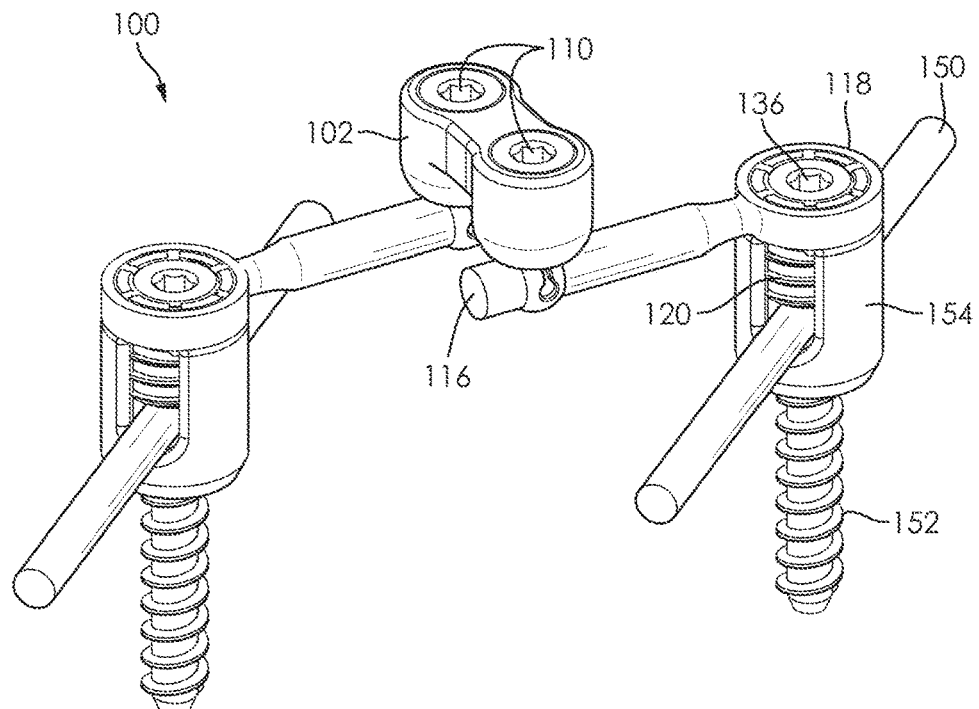
FIG. 14 is an illustration of an articulating spinal crosslink apparatus with a double joint attached to the heads of two pedicle screws of a spinal fusion construct in accordance with an embodiment of the present invention.

Turning now to FIG. 14, an illustration of an articulating spinal crosslink apparatus with a double joint attached to the heads of two pedicle screws of a spinal fusion construct in accordance with an embodiment of the present invention. In a preferred embodiment, the articulating spinal crosslink apparatus 100 is connected to two pedicle screws 152 of a spinal fusion construct. The crosslink arms 116 extend from the main body 102 of the articulating spinal crosslink apparatus 100 to connect with the pedicle screw heads 154. The crosslink arms are attached to the pedicle screws 152 via an expandable collet 120. In practice, the pedicle screw 152 will first be implanted into the patient that is undergoing spinal fusion surgery, followed by the placement of a spinal fusion rod 150 in the groove of the pedicle screw head 154. Next, the lower portion of the expandable collet 120 is secured to the pedicle screw head 154 using an internal driver feature (not shown) formed in the bottom center of the expandable collet 120. This will lock the spinal fusion rod 150 in place within the pedicle screw head 154. Then, the attachment collar 118 of a crosslink arm 116 is placed over and around the upper portion of the expandable collet 120. Subsequently, the collet securing means 136 is attached to the upper portion of the expandable collet 120 to secure the expandable collet 120 within the attachment collar 118. Finally, the joint locking elements 110 can be tightened to secure the crosslink arms 116 of the articulating spinal crosslink apparatus 100.

Figure 15:
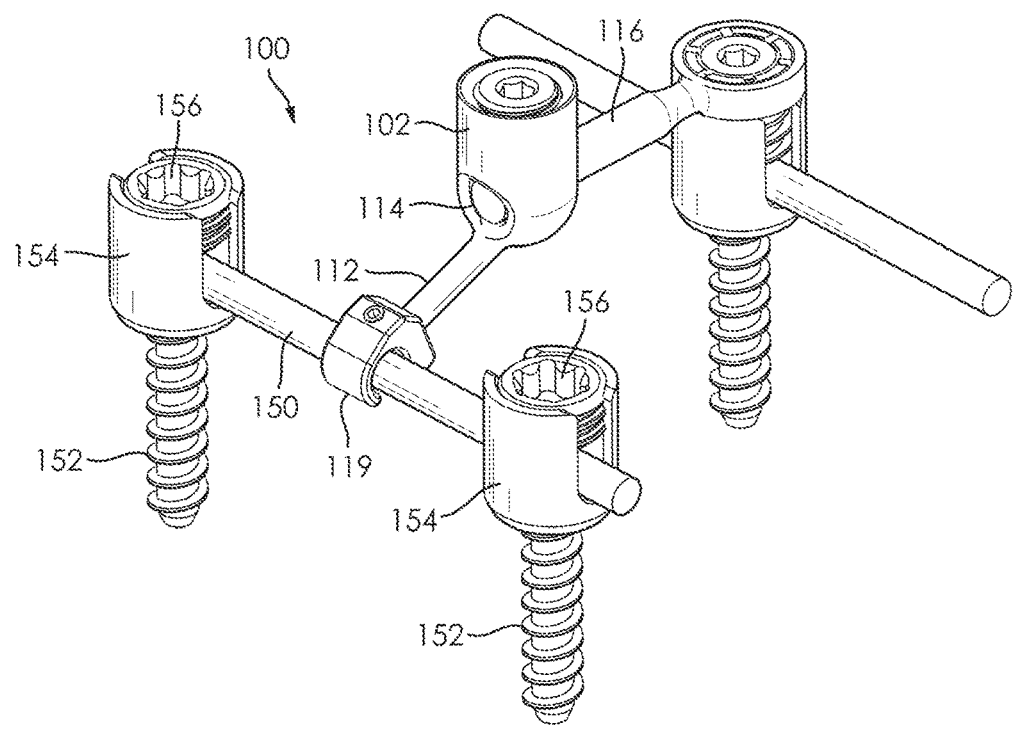
FIG. 15 is an illustration of an articulating spinal crosslink apparatus with a single joint with one crosslink arm attached to the head of a pedicle screw and the other crosslink arm connected directly to the rod of a spinal fusion construct via a hooked connector in accordance with an embodiment of the present invention.

Turning now to FIG. 15, an illustration of an articulating spinal crosslink apparatus with a single joint with one crosslink arm attached to the head of a pedicle screw and the other crosslink arm connected directly to the rod of a spinal fusion construct via a hooked connector in accordance with an embodiment of the present invention. In a preferred embodiment, the articulating spinal crosslink apparatus 100 is connected to one pedicle screw 152 on one side of a spinal fusion construct and directly to the spinal fusion rod on the other side. One crosslink arm 116 extends from the main body 102 of the articulating spinal crosslink apparatus 100 to connect with the pedicle screw head 154. The crosslink arm 116 is secured to the pedicle screw head 154 in the same manner described above. On the other side, the crosslink arm 112 includes a hooked connector 119 at the end of the crosslink arm 112 that is opposite the main joint body 102. The hooked connector 119 connects directly to a spinal fusion rod 150 that is already being held in place by pedicle screws 152. The hooked connector 119 is secured to the spinal fusion rod 150 using a set screw on the hooked connector 119. The spinal fusion rod 150 is held within a grove in the pedicle screw heads 154 and firmly secured by set screws 156 that are fastened to the pedicle screw heads 154. Lastly, the joint locking element 110 can be tightened to secure the crosslink arms 112, 116 of the articulating spinal crosslink apparatus 100.

It should be noted that the features illustrated in the drawings are not necessarily drawn to scale, and features of one embodiment may be employed with other embodiments as the skilled artisan would recognize, even if not explicitly stated herein. Descriptions of well-known components may be omitted so as to not unnecessarily obscure the embodiments.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature and not restrictive.

The invention claimed is:

1. A crosslink apparatus for linking a pair of rods in a spinal fusion construct, said crosslink apparatus comprising:
    a double joint main body with dual opposing receptacles, each receptacle having a top opening, a smaller bottom opening, and a continuous interior wall;
    a first crosslink arm;
    a second crosslink arm;
    wherein each of said crosslink arms comprise:
        an attachment collar adapted to receive an expandable collet; and
        a collet securing means that fastens to said expandable collet to cause said expandable collet to engage with said attachment collar;
    a pair of ball joint connectors, each comprising a bead portion and a body portion in the form of a crosslink arm connector;
    wherein each receptacle is configured to receive one of the ball joint connectors,
    wherein when the ball joint connectors are seated in their respective receptacles, the body portion of each ball joint connector extends through the bottom opening in each receptacle, but the head portion is too large to extend therethrough;
    wherein each crosslink arm connector that extends through the bottom opening, of its respective receptacle has an annular opening through which one of the crosslink anus extends, said opening being dimensioned to allow the crosslink arm connector to clamp around the crosslink arm.

2. The crosslink apparatus of claim 1, wherein an interior of each receptacle defines a ball joint socket configured to retain the head portion of the ball joint connector therein while allowing the body portion of the ball joint connector to extend outside of the receptacle.

3. The crosslink apparatus of claim 2, wherein each of said crosslink arms adjustably slides through its corresponding crosslink arm connector.

4. The crosslink apparatus of claim 3, further comprising a pair of joint locking elements, wherein each joint locking element is a joint set screw configured to rotatively engage with interior threading of one of the receptacles in order to secure said crosslink arms in place via said ball joint connectors.

5. The crosslink apparatus of claim 1, wherein said expandable collet is comprised of an upper portion configured with internal threading and a lower portion configured with external threading.

6. The crosslink apparatus of claim 5, wherein said upper portion of said expandable collet has a curved external surface.

7. The crosslink apparatus of claim 5, wherein said upper portion of said expandable collet is divided into a plurality of sections that expand to engage with said attachment collar when said collet securing means is a fastened to said expandable collet.

8. The crosslink apparatus of claim 1, wherein said expandable collet is comprised of an internal driver feature formed within said expandable collet.

9. The crosslink apparatus of claim 1, wherein said collet securing means is a collet set screw that expands said expandable collet to engage with said attachment collar.

10. A crosslink apparatus for linking a pair of rods in a spinal fusion construct, said crosslink apparatus comprising:
    a double joint main body with dual opposing receptacles, each receptacle having a top opening, a smaller bottom opening, and a continuous interior wall;
    a first crosslink arm;
    a second crosslink arm;
    a pair of ball joint connectors, each comprising a head portion and a body portion in the form of a crosslink arm connector;
    wherein each receptacle is configured to receive one of the ball joint connectors,
    wherein when the ball joint connectors are seated m their respective receptacles, the body portion of each ball joint, connector extends through the bottom opening, in each receptacle, but the head portion is too large to extend therethrough,
    wherein each crosslink arm connector has an opening through which one of the crosslink arms extends, said opening being dimensioned to allow the crosslink arm connector to clamp around the crosslink arm.

* * * * *